(12) United States Patent
Sato et al.

(10) Patent No.: US 12,179,178 B2
(45) Date of Patent: Dec. 31, 2024

(54) HYDROCARBON REFORMING CATALYST AND HYDROCARBON REFORMING APPARATUS

(71) Applicant: Murata Manufacturing Co., Ltd., Nagaokakyo (JP)

(72) Inventors: Hideto Sato, Nagaokakyo (JP); Akihiro Takeuchi, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 421 days.

(21) Appl. No.: 17/551,293

(22) Filed: Dec. 15, 2021

(65) Prior Publication Data

US 2022/0105495 A1 Apr. 7, 2022

Related U.S. Application Data

(63) Continuation of application No. PCT/JP2020/019744, filed on May 19, 2020.

(30) Foreign Application Priority Data

Aug. 1, 2019 (JP) .................................. 2019-142202

(51) Int. Cl.
| | |
|---|---|
| *B01J 23/00* | (2006.01) |
| *B01J 23/46* | (2006.01) |
| *B01J 23/58* | (2006.01) |
| *B01J 23/63* | (2006.01) |
| *C07C 1/04* | (2006.01) |

(52) U.S. Cl.
CPC ............. *B01J 23/63* (2013.01); *B01J 23/002* (2013.01); *B01J 23/58* (2013.01); *C07C 1/0435* (2013.01); *C07C 2523/58* (2013.01); *C07C 2523/63* (2013.01)

(58) Field of Classification Search
CPC ........ B01J 23/002; B01J 23/462; B01J 23/58; B01J 23/63; C07C 1/0435; C07C 2523/58; C07C 2523/63
See application file for complete search history.

(56) References Cited

U.S. PATENT DOCUMENTS 10,407,620 B2 * 9/2019 Gu ........................... C10G 9/16
10,486,143 B2 * 11/2019 Li .......................... B01J 23/745
(Continued)

FOREIGN PATENT DOCUMENTS

| AU | 6182199 A | 4/2000 |
|---|---|---|
| JP | H08231204 A | 9/1996 |

(Continued)

OTHER PUBLICATIONS

International Search Report issued for PCT/JP2020/019744, date of mailing Aug. 11, 2020.

(Continued)

*Primary Examiner* — Cam N. Nguyen
(74) *Attorney, Agent, or Firm* — ArentFox Schiff LLP

(57) ABSTRACT

A hydrocarbon reforming catalyst for forming a synthetic gas containing hydrogen and carbon monoxide from a hydrocarbon-based gas, the hydrocarbon reforming catalyst containing a complex oxide having a perovskite structure, the complex oxide having at least a first crystal phase containing $BaCeO_3$ as a primary component and also containing Ru.

18 Claims, 2 Drawing Sheets

(56) References Cited

U.S. PATENT DOCUMENTS

| | | | |
|---|---|---|---|
| 11,668,012 B2* | 6/2023 | Ding | C25B 3/00 |
| | | | 205/462 |
| 11,731,920 B2* | 8/2023 | Ding | C25B 13/07 |
| | | | 205/462 |
| 11,958,746 B2* | 4/2024 | Sato | B01J 35/733 |
| 2008/0169449 A1 | 7/2008 | Mundschau | |
| 2016/0369174 A1 | 12/2016 | Kool et al. | |
| 2017/0001913 A1* | 1/2017 | Zhou | B01J 23/10 |

FOREIGN PATENT DOCUMENTS

| | | | |
|---|---|---|---|
| JP | H09168740 A | 6/1997 |
| JP | 2006346598 A | 12/2006 |
| JP | 2010110697 A | 5/2010 |
| JP | 2015136668 A | 7/2015 |
| JP | 2017509732 A | 4/2017 |
| WO | 2004074175 A1 | 9/2004 |

OTHER PUBLICATIONS

Ruocco et al., "Methane dry reforming on Ru perovskites, AZr-RuO3: Influence of preparation method and substitution of A cation with alkaline earth metals," Journal of CO2 Utilization, 2019, vol. 30, pp. 222-231.

Shimoda et al., "Ammonia synthesis over yttrium-doped barium zirconate and cerate-based perovskite-type oxide supported ruthenium catalysts," International Journal of Hydrogen Energy, 2017, vol. 42, pp. 29745-29755.

\* cited by examiner

HYDROCARBON REFORMING CATALYST AND HYDROCARBON REFORMING APPARATUS

CROSS REFERENCE TO RELATED APPLICATIONS

The present application is a continuation of International application No. PCT/JP2020/019744, filed May 19, 2020, which claims priority to Japanese Patent Application No. 2019-142202, filed Aug. 1, 2019, the entire contents of each of which are incorporated herein by reference.

FIELD OF THE INVENTION

The present invention relates to a hydrocarbon reforming catalyst used for forming a synthetic gas containing hydrogen and carbon monoxide from a hydrocarbon-based gas, and to a hydrocarbon reforming apparatus including the hydrocarbon reforming catalyst.

BACKGROUND OF THE INVENTION

In a known method, a synthetic gas containing hydrogen and carbon monoxide is obtained from a hydrocarbon-based gas by using a catalyst. Examples of the known catalyst used for a reforming reaction of the hydrocarbon-based gas include nickel-based catalysts in which nickel is supported by a base substrate such as alumina, ruthenium-based catalysts in which ruthenium is supported (refer to Patent Document 1), and rhodium-based catalysts in which rhodium is supported by a base substrate such as alumina (refer to Patent Document 2).

Further, in known catalysts, rhodium, cobalt, or nickel serving as an active component is supported by a carrier including lanthanum aluminate, strontium titanate, or barium titanate, which are perovskite-type compounds, to suppress carbon from depositing and to improve the activity at low temperature (refer to Patent Document 3).

As a common method for producing a metal-supporting catalyst, an impregnation method in which an active metal is dispersed on the carrier surface by dipping an oxide serving as a carrier into a solution of a metal salt or the like and, thereafter, performing heat treatment is used (Patent Document 1 to Patent Document 3).

In this regard, the carrier component is required to have high heat stability and strength and, therefore, is sufficiently sintered by being subjected to heat treatment at high temperature, while the dispersibility of the supported metal has to be maintained to obtain high activity. Consequently, to minimize aggregation during a heat treatment step, the supported metal is fixed to the carrier under a heat treatment at a relatively low temperature by using a production step different from the synthesis of the carrier, as in the impregnation method.

The catalyst produced by the impregnation method can maintain high metal dispersibility. However, the impregnation step of supporting the metal component is necessary in addition to the carrier component synthesis step. Further, since the metal component is made to adhere by heat treatment at a relatively low temperature, coupling between the metal and the carrier is weak, and carbon deposition may cause activity deterioration problems.

Consequently, as a method for producing a catalyst without using the impregnation step, a method in which a complex oxide containing $BaNiY_2O_5$ is synthesized through solid-phase synthesis so as to improve the dispersibility of a Ni component is proposed (Patent Document 4).

Patent Document 1: Japanese Unexamined Patent Application Publication No. 8-231204
Patent Document 2: Japanese Unexamined Patent Application Publication No. 9-168740
Patent Document 3: Japanese Unexamined Patent Application Publication No. 2006-346598
Patent Document 4: Japanese Unexamined Patent Application Publication No. 2015-136668

SUMMARY OF THE INVENTION

The catalyst described in Patent Document 4 can suppress carbon deposition. However, the activity is not sufficiently high, and there is therefore room for improvement.

The present invention addresses the above-described problem, and it is an object thereof to provide a hydrocarbon reforming catalyst having high activity and to provide a hydrocarbon reforming apparatus including such a hydrocarbon reforming catalyst.

A hydrocarbon reforming catalyst according to the present invention is a catalyst for forming a synthetic gas containing hydrogen and carbon monoxide from a hydrocarbon-based gas, the hydrocarbon reforming catalyst containing a complex oxide having a perovskite structure, the complex oxide having at least a first crystal phase containing $BaCeO_3$ as a primary component and also containing Ru.

According to the present invention, a hydrocarbon reforming catalyst having high activity and a hydrocarbon reforming apparatus including such a hydrocarbon reforming catalyst are provided.

DETAILED DESCRIPTION OF THE PREFERRED EMBODIMENTS

An embodiment according to the present invention will be illustrated below so as to specifically describe certain features of the present invention.

The hydrocarbon reforming catalyst according to the present invention is a catalyst used for forming a synthetic gas containing hydrogen and carbon monoxide from a hydrocarbon-based gas. The hydrocarbon reforming catalyst contains a complex oxide having a perovskite structure, wherein the complex oxide has a crystal phase containing $BaCeO_3$ as a primary component and contains Ru (hereafter referred to as requirements of the present invention).

A propane gas containing propane as a primary component or a natural gas containing methane as a primary component may be used as the hydrocarbon-based gas that is a treatment object gas. In addition, hydrocarbon-based gases obtained by vaporizing liquid hydrocarbons, such as gasoline, kerosene, methanol, and ethanol, may also be used.

The reaction which forms a synthetic gas containing hydrogen and carbon monoxide from a hydrocarbon-based gas will be described with reference to steam reforming of a propane gas as an example. The steam reforming of a propane gas is represented by formula (1) below.

$$C_3H_8 + 3H_2O \rightarrow 7H_2 + 3CO \qquad (1)$$

In this regard, the method for forming a synthetic gas containing hydrogen and carbon monoxide from a hydrocarbon-based gas is not limited to steam reforming. For example, oxygen, carbon dioxide, or a mixture thereof may be contained instead of steam. When carbon dioxide is contained, the reforming reaction is represented by formula (2) below.

$$C_3H_8 + 3CO_2 \rightarrow 4H_2 + 6CO \qquad (2)$$

Figure 1:
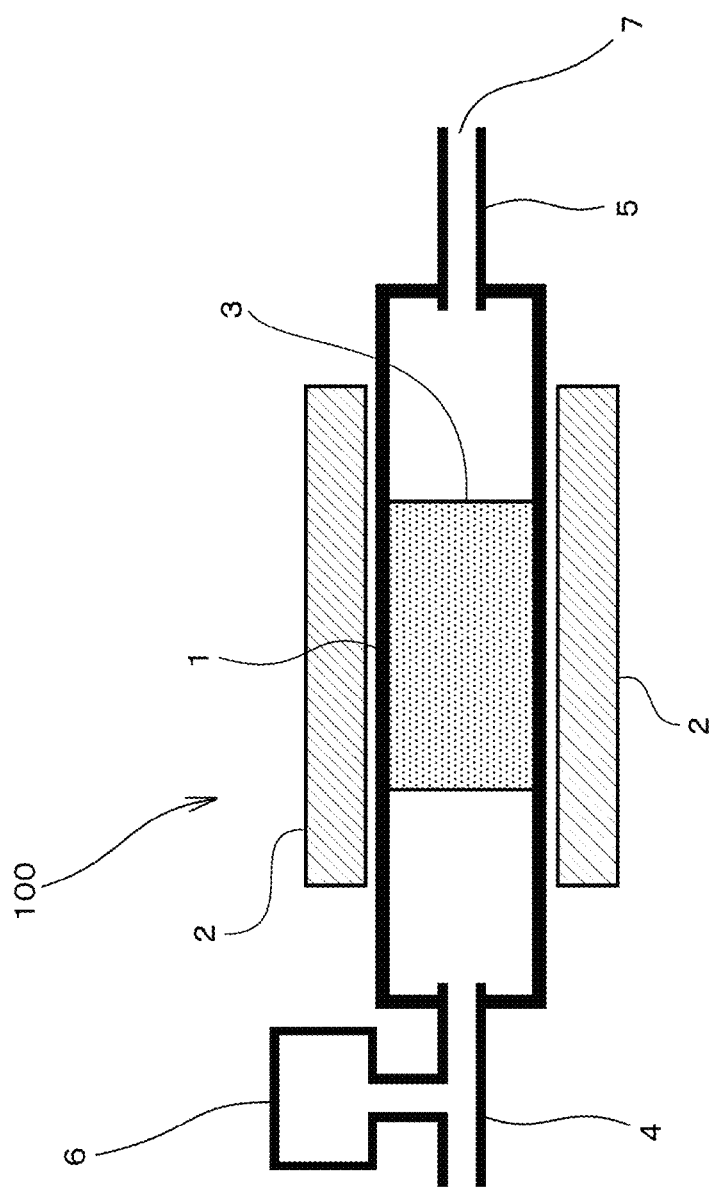
FIG. 1 is a diagram illustrating the outline of the configuration of a hydrocarbon reforming apparatus.

FIG. 1 is a diagram illustrating the outline of the configuration of a hydrocarbon reforming apparatus 100 to form a synthetic gas containing hydrogen and carbon monoxide from a treatment object gas containing at least a hydrocarbon. The hydrocarbon reforming apparatus 100 includes a pipe 1 through which the treatment object gas passes, a heating portion 2 to heat the treatment object gas passing through the pipe 1, and a hydrocarbon reforming catalyst 3 disposed at a position in contact with the treatment object gas inside the pipe 1. The hydrocarbon reforming catalyst 3 is a catalyst that satisfies the requirements of the present invention and contains a complex oxide having a perovskite structure, and the complex oxide has a crystal phase containing $BaCeO_3$ as a primary component and also containing Ru. In this regard, when just the treatment object gas is at a sufficiently high temperature, the heating portion 2 may be skipped.

A gas feed pipe 4 is coupled to the upstream side of the pipe 1. A hydrocarbon is fed from a hydrocarbon supply source 6 to the gas feed pipe 4. However, the hydrocarbon supply source 6 may be disposed at the former stage of the gas feed pipe 4. In this regard, the hydrocarbon fed from the hydrocarbon supply source 6 may contain other components.

A gas discharge pipe 5 to discharge a synthetic gas containing hydrogen and carbon monoxide obtained through reforming is coupled to the downstream side of the pipe 1. The gas discharge pipe 5 is provided with a hydrogen outlet 7 and is configured to be capable of separating hydrogen contained in the synthetic gas. For example, a CO converter may be disposed in the gas discharge pipe 5 so as to remove carbon monoxide contained in the synthetic gas, and hydrogen may be separated through the hydrogen outlet 7.

Examples 1 to 24

$BaCO_3$, $ZrO_2$, $CeO_2$, $Y_2O_3$, and $RuO_2$ were prepared as the materials for forming the hydrocarbon reforming catalyst and weighed so that the molar ratio of Ba:Zr:Ce:Y:Ru was set to be equal to the ratio described in Table 1, and pebbles, water, and a binder were wet-mixed so as to obtain a mixture. The resulting mixture was dried in an oven at a temperature of 120° C. and was pulverized and classified so as to have a granular shape with the size of 0.5 mm to 0.7 mm. Thereafter, hydrocarbon reforming catalysts of examples 1 to 24 were obtained by firing the granular sample in air under the conditions of 1,000° C. and 1 hour.

The hydrocarbon reforming catalysts of examples 1 to 24 are catalysts satisfying the requirements of the present invention. As described in Table 1, the hydrocarbon reforming catalysts of examples 1 to 24 contain Ba, Zr, Ce, Y, and Ru. The molar ratio of Ce to Ba is 0.10 to 0.70, the molar ratio of Ru to Ba is 0.04 to 0.43, the molar ratio of Y to Ba is 0.05 to 0.50, and the molar ratio of Zr to Ba is 0.10 to 0.80. In addition, the molar ratio of a total amount of Zr, Ce, and Y to Ba is 0.71 to 1.67.

Examples 25 to 28

Regarding the material for forming the hydrocarbon reforming catalyst, $BaCO_3$, $ZrO_2$, $CeO_2$, and $RuO_2$ were prepared and weighed so that the molar ratio of Ba:Zr:Ce:Ru was set to be equal to the ratio described in Table 1, and pebbles, water, and a binder were wet-mixed so as to obtain a mixture. Thereafter, hydrocarbon reforming catalysts of examples 25 to 28 were produced by using the same method as the method for producing the hydrocarbon reforming catalysts of examples 1 to 24.

The hydrocarbon reforming catalysts of examples 25 to 28 are catalysts satisfying the requirements of the present invention. As described in Table 1, the hydrocarbon reforming catalysts of examples 25 to 28 contain Ba, Zr, Ce, and Ru.

Examples 29 to 32

Regarding the material for forming the hydrocarbon reforming catalyst, $BaCO_3$, $CeO_2$, $Y_2O_3$, and $RuO_2$ were prepared and weighed so that the molar ratio of Ba:Ce:Y:Ru was set to be equal to the ratio described in Table 1, and pebbles, water, and a binder were wet-mixed so as to obtain a mixture. Thereafter, hydrocarbon reforming catalysts of examples 29 to 32 were produced by using the same method as the method for producing the hydrocarbon reforming catalysts of examples 1 to 24.

The hydrocarbon reforming catalysts of examples 29 to 32 are catalysts satisfying the requirements of the present invention. As described in Table 1, the hydrocarbon reforming catalysts of examples 29 to 32 contain Ba, Ce, Y, and Ru.

Example 33

Regarding the material for forming the hydrocarbon reforming catalyst, $BaCO_3$, $CeO_2$, and $RuO_2$ were prepared and weighed so that the molar ratio of Ba:Ce:Ru was set to equal to the ratio described in Table 1, and pebbles, water, and a binder were wet-mixed so as to obtain a mixture. Thereafter, a hydrocarbon reforming catalyst of example 33 was produced by using the same method as the method for producing the hydrocarbon reforming catalysts of examples 1 to 24.

The hydrocarbon reforming catalyst of example 33 is a catalyst satisfying the requirements of the present invention. As described in Table 1, the hydrocarbon reforming catalyst of example 33 contains Ba, Ce, and Ru.

In this regard, in the production steps of the hydrocarbon reforming catalysts of examples 1 to 33, the impregnation step to make the carrier to support a metal component is unnecessary.

Comparative Example 1

Regarding the material for forming the hydrocarbon reforming catalyst, $BaCO_3$, $ZrO_2$, $CeO_2$, and $RuO_2$ were prepared and weighed so that the molar ratio of Ba:Zr:Ce:Ru was set to be equal to the ratio described in Table 1, and pebbles, water, and a binder were wet-mixed so as to obtain a mixture. The molar ratio of Ba:Zr:Ce:Ru in the resulting mixture was equal to the molar ratio of the materials used for producing the hydrocarbon reforming catalyst of example 26. Thereafter, a hydrocarbon reforming catalyst of comparative example 1 was produced by using the same method as the method for producing the hydrocarbon reforming catalyst of example 26 except that the firing temperature was set to be 500° C. The hydrocarbon reforming catalyst of comparative example 1 is a catalyst not satisfying the requirements of the present invention.

Comparative Example 2

Regarding the material for forming the hydrocarbon reforming catalyst, $BaCO_3$, $ZrO_2$, $CeO_2$, $Y_2O_3$, and $RuO_2$ were prepared and weighed so that the molar ratio of Ba:Zr:Ce:Y:Ru was set to be equal to the ratio described in Table 1, and pebbles, water, and a binder were wet-mixed so as to obtain a mixture. The molar ratio of Ba:Zr:Ce:Y:Ru in the resulting mixture was equal to the molar ratio of the materials used for producing the hydrocarbon reforming catalyst of example 2. Thereafter, a hydrocarbon reforming catalyst of comparative example 2 was produced by using the same method as the method for producing the hydrocarbon reforming catalyst of example 2 except that the firing temperature was set to be 500° C. The hydrocarbon reforming catalyst of comparative example 2 is a catalysts not satisfying the requirements of the present invention.

<Examination of Crystal Phase>

The hydrocarbon reforming catalysts of examples 1 to 33 and comparative examples 1 and 2 above were pulverized by using a mortar, and the crystal phase was examined by powder XRD measurement. Regarding the powder XRD measurement, Cu-Kα1 was used as the X-ray.

Table 1 describes the crystal phase and the composition (molar ratio) examined with respect to the hydrocarbon reforming catalysts of examples 1 to 33 and comparative examples 1 and 2.

Regarding the hydrocarbon reforming catalysts of examples 1 to 33, it was ascertained that a crystal phase of a complex oxide having a perovskite structure, specifically, a crystal phase containing $BaCeO_3$ as a primary component was present. Further, regarding the hydrocarbon reforming catalysts of examples 1 to 28, it was ascertained that a crystal phase containing $BaCeO_3$ as a primary component and a crystal phase containing $BaZrO_3$ as a primary component were present.

Regarding hydrocarbon reforming catalysts of some examples, heterogeneous phases such as $BaCO_3$ and $Y_2O_3$ were also observed in accordance with the composition ratio. However, even in these hydrocarbon reforming catalysts, the main crystal phase of the complex oxide having a perovskite structure is a crystal phase containing $BaCeO_3$ as a primary component when a crystal phase containing $BaZrO_3$ as a primary component is not contained, and the main crystal phase of the complex oxide having the perovskite structure is a first crystal phase containing $BaCeO_3$ as a primary component and a second crystal phase containing $BaZrO_3$ as a primary component when a crystal phase containing $BaZrO_3$ as a primary component is contained therein.

Figure 2:
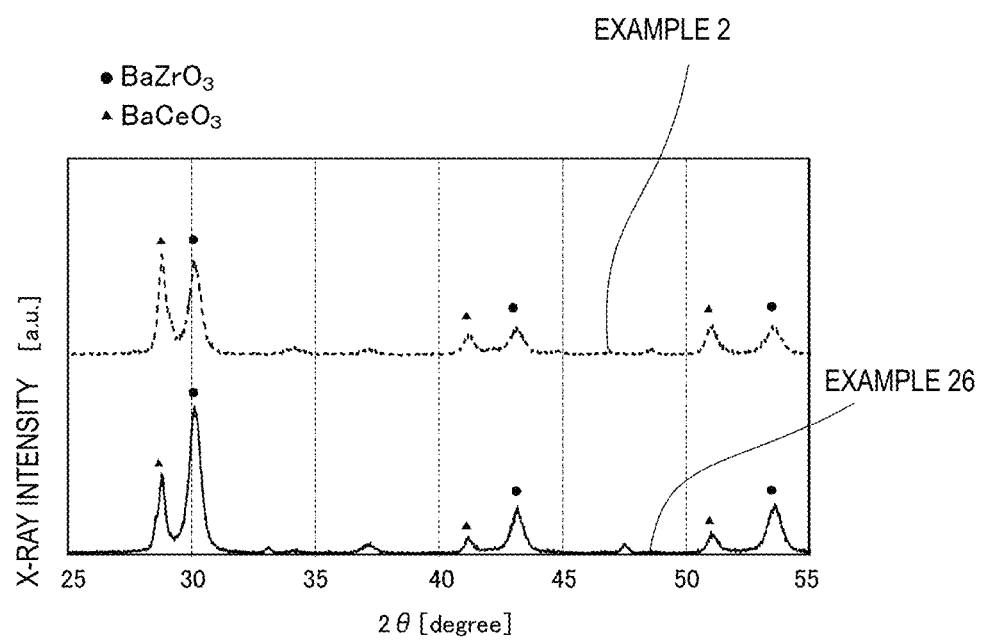
FIG. 2 is a diagram illustrating X-ray diffraction patterns of the hydrocarbon reforming catalysts of example 2 and example 26.

FIG. 2 illustrates X-ray diffraction patterns of the hydrocarbon reforming catalysts of example 2 and example 26. As illustrated in FIG. 2, it can be ascertained that a crystal phase containing $BaZrO_3$ as a primary component and a crystal phase containing $BaCeO_3$ as a primary component are present in the hydrocarbon reforming catalysts of example 2 and example 26. On the other hand, no diffraction lines attributed to $RuO_2$ and Ru simple substance were observed. Regarding the hydrocarbon reforming catalyst of example 2 in which $Y_2O_3$ was contained in the raw material when the catalyst was produced, no diffraction lines attributed to $Y_2O_3$ were observed.

TABLE 1

| Catalyst | Crystal phase | Molar ratio | | | | |
| --- | --- | --- | --- | --- | --- | --- |
| | | Ba | Zr | Ce | Y | Ru |
| Example 1 | $BaZrO_3$, $BaCeO_3$ | 1.00 | 0.40 | 0.30 | 0.30 | 0.04 |
| Example 2 | $BaZrO_3$, $BaCeO_3$ | 1.00 | 0.40 | 0.30 | 0.30 | 0.09 |
| Example 3 | $BaZrO_3$, $BaCeO_3$ | 1.00 | 0.40 | 0.30 | 0.30 | 0.13 |
| Example 4 | $BaZrO_3$, $BaCeO_3$ | 1.00 | 0.40 | 0.30 | 0.30 | 0.22 |
| Example 5 | $BaZrO_3$, $BaCeO_3$ | 1.00 | 0.40 | 0.30 | 0.30 | 0.43 |
| Example 6 | $BaZrO_3$, $BaCeO_3$ | 1.00 | 0.65 | 0.30 | 0.05 | 0.09 |
| Example 7 | $BaZrO_3$, $BaCeO_3$ | 1.00 | 0.60 | 0.30 | 0.10 | 0.09 |
| Example 8 | $BaZrO_3$, $BaCeO_3$ | 1.00 | 0.50 | 0.30 | 0.20 | 0.09 |
| Example 9 | $BaZrO_3$, $BaCeO_3$ | 1.00 | 0.30 | 0.30 | 0.40 | 0.09 |
| Example 10 | $BaZrO_3$, $BaCeO_3$ | 1.00 | 0.20 | 0.30 | 0.50 | 0.09 |
| Example 11 | $BaZrO_3$, $BaCeO_3$ | 1.00 | 0.60 | 0.10 | 0.30 | 0.08 |
| Example 12 | $BaZrO_3$, $BaCeO_3$ | 1.00 | 0.50 | 0.20 | 0.30 | 0.09 |
| Example 13 | $BaZrO_3$, $BaCeO_3$ | 1.00 | 0.30 | 0.40 | 0.30 | 0.09 |
| Example 14 | $BaZrO_3$, $BaCeO_3$ | 1.00 | 0.20 | 0.50 | 0.30 | 0.09 |
| Example 15 | $BaZrO_3$, $BaCeO_3$ | 1.00 | 0.10 | 0.50 | 0.40 | 0.09 |
| Example 16 | $BaZrO_3$, $BaCeO_3$, $BaCO_3$ | 1.00 | 0.10 | 0.70 | 0.20 | 0.09 |
| Example 17 | $BaZrO_3$, $BaCeO_3$, $BaCO_3$ | 1.00 | 0.20 | 0.70 | 0.10 | 0.09 |
| Example 18 | $BaZrO_3$, $BaCeO_3$, $Y_2O_3$, $BaCO_3$ | 1.00 | 0.20 | 0.30 | 0.50 | 0.09 |
| Example 19 | $BaZrO_3$, $BaCeO_3$, $Y_2O_3$, $BaCO_3$ | 1.00 | 0.40 | 0.10 | 0.50 | 0.08 |
| Example 20 | $BaZrO_3$, $BaCeO_3$ | 1.00 | 0.80 | 0.10 | 0.10 | 0.08 |
| Example 21 | $BaZrO_3$, $BaCeO_3$, $BaCO_3$ | 1.00 | 0.67 | 0.50 | 0.50 | 0.11 |
| Example 22 | $BaZrO_3$, $BaCeO_3$, $BaCO_3$ | 1.00 | 0.50 | 0.38 | 0.38 | 0.10 |
| Example 23 | $BaZrO_3$, $BaCeO_3$, $BaCO_3$ | 1.00 | 0.33 | 0.25 | 0.25 | 0.08 |
| Example 24 | $BaZrO_3$, $BaCeO_3$, $BaCO_3$ | 1.00 | 0.29 | 0.21 | 0.21 | 0.08 |
| Example 25 | $BaZrO_3$, $BaCeO_3$, $BaCO_3$ | 1.00 | 0.80 | 0.20 | — | 0.09 |
| Example 26 | $BaZrO_3$, $BaCeO_3$, $BaCO_3$ | 1.00 | 0.70 | 0.30 | — | 0.09 |
| Example 27 | $BaZrO_3$, $BaCeO_3$, $BaCO_3$ | 1.00 | 0.50 | 0.50 | — | 0.09 |
| Example 28 | $BaZrO_3$, $BaCeO_3$, $BaCO_3$ | 1.00 | 0.30 | 0.70 | — | 0.09 |
| Example 29 | $BaCeO_3$, $Y_2O_3$, $BaCO_3$ | 1.00 | — | 0.30 | 0.70 | 0.09 |
| Example 30 | $BaCeO_3$, $Y_2O_3$, $BaCO_3$ | 1.00 | — | 0.50 | 0.50 | 0.09 |
| Example 31 | $BaCeO_3$, $Y_2O_3$, $BaCO_3$ | 1.00 | — | 0.70 | 0.30 | 0.09 |
| Example 32 | $BaCeO_3$, $Y_2O_3$, $BaCO_3$ | 1.00 | — | 0.90 | 0.10 | 0.10 |
| Example 33 | $BaCeO_3$ | 1.00 | — | 1.00 | — | 0.10 |
| Comparative example 1 | $BaCO_3$, $ZrO_2$, $CeO_2$, $RuO_2$ | 1.00 | 0.70 | 0.30 | — | 0.09 |
| Comparative example 2 | $BaCO_3$, $ZrO_2$, $CeO_2$, $Y_2O_3$, $RuO_2$ | 1.00 | 0.40 | 0.30 | 0.30 | 0.09 |

That is, each of Y and Ru is present in at least one structure of a crystal phase containing $BaZrO_3$ as a primary component and a crystal phase containing $BaCeO_3$ as a primary component. In other words, each of Y and Ru is present as a component constituting a complex oxide having a perovskite structure.

Likewise, each of Y and Ru is present as a component constituting a complex oxide having a perovskite structure in the hydrocarbon reforming catalysts of examples 1, 3 to 24, and 29 to 32. Regarding the hydrocarbon reforming catalysts of examples 25 to 28 and 33 in which Y is not contained in a complex oxide, Ru is present as a component constituting the complex oxide having a perovskite structure.

The perovskite structure of the complex oxide constituting the hydrocarbon reforming catalyst of each example will be described. In the hydrocarbon reforming catalysts of examples 1 to 24, the perovskite structure is composed of at least Ba, Zr, Ce, Y, and Ru. In the hydrocarbon reforming catalysts of examples 25 to 28, the perovskite structure is composed of at least Ba, Zr, Ce, and Ru. In the hydrocarbon reforming catalysts of examples 29 to 32, the perovskite structure is composed of at least Ba, Ce, Y, and Ru. In the hydrocarbon reforming catalyst of example 33, the perovskite structure is composed of at least Ba, Ce, and Ru.

On the other hand, it was ascertained that the hydrocarbon reforming catalyst of comparative example 1 was a mixture of $BaCO_3$, $ZrO_2$, $CeO_2$, and $RuO_2$ that were used for preparation since the firing temperature during production was 500° C. which was lower than the formation temperature of the complex oxide having a perovskite structure. Likewise, it was ascertained that the hydrocarbon reforming catalyst of comparative example 2 was also a mixture of $BaCO_3$, $ZrO_2$, $CeO_2$, $Y_2O_3$, and $RuO_2$ that were used for preparation.

<Examination of Composition>

The hydrocarbon reforming catalysts of examples 1 to 33 and the hydrocarbon reforming catalysts of comparative examples 1 and 2 were finely pulverized by using a mortar, and the resulting powders were subjected to composition analysis by X-ray fluorescence analysis (XRF analysis). As a result, it was ascertained that regarding all the hydrocarbon reforming catalysts subjected to the composition analysis, the element molar ratio of formulation for weighing was maintained and a change in element molar ratio, such as a reduction in the Ru component due to heating and firing treatment, did not occur.

In this regard, when a common Ru-based catalyst is heated at high temperature in an atmosphere containing oxygen, a Ru component is converted to $RuO_4$ and is sublimated so that the Ru content is decreased. However, regarding the hydrocarbon reforming catalysts of examples 1 to 33 satisfying the requirements of the present invention, it is believed that since Ru is present in the structure of at least one of a crystal phase containing $BaZrO_3$ as a primary component and a crystal phase containing $BaCeO_3$ as a primary component, the above-described reduction in Ru does not occur.

<Evaluation of Reforming>

The hydrocarbon reforming catalyst of each of examples 1 to 33 and comparative examples of 1 and 2 was pulverized and classified into the size of 0.5 mm to 0.7 mm. Thereafter, a steam reforming evaluation test of a propane gas which is a hydrocarbon-based gas was performed.

The pipe 1 of the hydrocarbon reforming apparatus 100 illustrated in FIG. 1 was filled with 0.3 g of hydrocarbon reforming catalyst produced by using the above-described method, and heating at 600° C. was performed in the heating portion 2. Subsequently, a raw material gas was introduced from the gas feed pipe 4 at a flow rate of nitrogen ($N_2$) of 360 cc/min, propane ($C_3H_8$) of 7 cc/min, steam ($H_2O$) of 60 cc/min, and carbon dioxide ($CO_2$) of 60 cc/min.

The raw material gas introduced into the pipe 1 was reformed, and a synthetic gas containing hydrogen and carbon monoxide was discharged from the gas discharge pipe 5. The synthetic gas discharged from the gas discharge pipe 5 was introduced into a gas analyzer (gas chromatograph) after moisture was removed by a cooling-type trap, and a hydrogen concentration was measured.

Herein, as a result of calculation of the equilibrium gas composition at the above-described conditions of the gas partial pressure and the temperature, the gas concentration percentage in an equilibrium state was 8.1% by volume except for moisture. Therefore, when the reaction of the introduced raw material gas progresses 100%, the concentration of hydrogen in an equilibrium state (hereafter referred to as an equilibrium hydrogen concentration) discharged from the gas discharge pipe 5 is 8.1% by volume.

(I) Examination of Initial Activity

It was assumed that no sulfur component was present for the first 1 hour from introduction of the raw material gas, and the hydrogen concentration after 1 hour was measured so as to examine the initial activity of the hydrocarbon reforming catalyst. Table 2 describes the concentration of hydrogen discharged from the gas discharge pipe 5 (initial hydrogen concentration) and the equilibrium achievement percentage of the initial activity when the hydrocarbon reforming catalyst of each of the examples and the comparative examples was used. The equilibrium achievement percentage of the initial activity was defined by formula (3) below.

equilibrium achievement percentage of initial activity=initial hydrogen concentration/equilibrium hydrogen concentration×100    (3)

(II) Examination of Characteristics after Deterioration Due to Sulfur

After the above-described initial activity was examined, a $SO_2$ gas was mixed so that the proportion was set to be 50 ppm relative to the total flow rate of the raw material gas of 487 cc/min, the hydrogen gas concentration after 1 hour was measured so as to examine deterioration in the catalyst activity in the presence of sulfur. Table 2 describes the concentration of hydrogen discharged from the gas discharge pipe 5 after 1 hour in the presence of sulfur and the equilibrium achievement percentage when the hydrocarbon reforming catalyst of each of the examples and the comparative examples was used. In Table 2, these are expressed as the hydrogen concentration "After deterioration due to sulfur" and "Equilibrium achievement percentage after deterioration due to sulfur". The equilibrium achievement percentage after deterioration due to sulfur was defined by formula (4) below.

equilibrium achievement percentage after deterioration due to sulfur=hydrogen concentration after deterioration due to sulfur/equilibrium hydrogen concentration×100    (4)

(III) Examination of Characteristics after Heat Treatment

After the above-described characteristics after deterioration due to sulfur were examined, the hydrocarbon reforming catalyst was heated to 700° C. while a flow rate of 360 cc/min of nitrogen ($N_2$), 60 cc/min of steam ($H_2O$), and 60 cc/min of carbon dioxide ($CO_2$) were introduced into the pipe 1, and heat treatment was successively performed for 1 hour. Thereafter, the temperature was lowered to 600° C., and a flow rate of 360 cc/min of nitrogen ($N_2$), 7 cc/min of propane ($C_3H_8$), 60 cc/min of steam ($H_2O$), and 60 cc/min of carbon dioxide ($CO_2$) were introduced again, and the hydrogen concentration after 1 hour was measured so as to examine the activity of the hydrocarbon reforming catalyst after heat treatment.

catalyst was cooled and removed in a $N_2$ atmosphere, and a change in the weight of the catalyst due to carbon combustion was examined by TG-DTA (thermogravimetric-differential thermal analysis). As a result, regarding all the hydrocarbon reforming catalysts of the examples and comparative examples subjected to the evaluation, carbon deposition was not observed.

TABLE 2

| Catalyst | Hydrogen concentration (% by volume) | | | Equilibrium achievement percentage of initial activity | Equilibrium achievement percentage after deterioration due to sulfur | Recovery factor due to heating |
|---|---|---|---|---|---|---|
| | Initial stage | After deterioration due to sulfur | After heat treatment | | | |
| Example 1 | 5.4 | 3.6 | 3.9 | 67% | 44% | 4% |
| Example 2 | 8.0 | 5.8 | 6.4 | 99% | 72% | 7% |
| Example 3 | 8.0 | 7.5 | 7.7 | 99% | 93% | 2% |
| Example 4 | 8.1 | 7.6 | 7.8 | 100% | 94% | 2% |
| Example 5 | 8.1 | 7.9 | 8.0 | 100% | 98% | 1% |
| Example 6 | 8.0 | 6.7 | 7.0 | 99% | 83% | 4% |
| Example 7 | 7.9 | 6.9 | 7.1 | 98% | 85% | 2% |
| Example 8 | 8.0 | 6.4 | 6.7 | 99% | 79% | 4% |
| Example 9 | 8.0 | 6.8 | 7.0 | 99% | 84% | 2% |
| Example 10 | 8.0 | 6.5 | 6.9 | 99% | 80% | 5% |
| Example 11 | 8.0 | 6.8 | 7.0 | 99% | 84% | 2% |
| Example 12 | 8.0 | 7.1 | 7.3 | 99% | 88% | 2% |
| Example 13 | 8.1 | 6.2 | 6.8 | 100% | 77% | 7% |
| Example 14 | 8.1 | 6.2 | 6.6 | 100% | 77% | 5% |
| Example 15 | 8.1 | 4.2 | 4.9 | 100% | 52% | 9% |
| Example 16 | 8.1 | 5.0 | 6.0 | 100% | 62% | 12% |
| Example 17 | 8.0 | 5.0 | 5.5 | 99% | 62% | 6% |
| Example 18 | 8.1 | 4.5 | 5.5 | 100% | 56% | 12% |
| Example 19 | 8.1 | 6.0 | 6.5 | 100% | 74% | 6% |
| Example 20 | 7.9 | 4.6 | 4.8 | 98% | 57% | 2% |
| Example 21 | 8.1 | 7.1 | 7.3 | 100% | 88% | 2% |
| Example 22 | 8.1 | 7.4 | 7.6 | 100% | 91% | 2% |
| Example 23 | 8.0 | 6.8 | 7.1 | 99% | 84% | 4% |
| Example 24 | 8.1 | 6.9 | 7.2 | 100% | 85% | 4% |
| Example 25 | 7.9 | 0.0 | 0.0 | 98% | 59% | −10% |
| Example 26 | 7.8 | 6.6 | 6.3 | 96% | 81% | −4% |
| Example 27 | 7.9 | 7.0 | 7.2 | 98% | 86% | 2% |
| Example 28 | 7.9 | 7.5 | 7.7 | 98% | 93% | 2% |
| Example 29 | 8.0 | 1.5 | 5.0 | 99% | 19% | 43% |
| Example 30 | 8.0 | 2.0 | 4.0 | 99% | 25% | 25% |
| Example 31 | 8.1 | 2.5 | 4.3 | 100% | 31% | 22% |
| Example 32 | 7.9 | 3.0 | 5.0 | 98% | 37% | 25% |
| Example 33 | 8.1 | 1.5 | 3.2 | 100% | 19% | 21% |
| Comparative example 1 | 2.6 | 0.0 | 0.0 | 32% | 0% | 0% |
| Comparative example 2 | 3.0 | 0.0 | 0.0 | 37% | 0% | 0% |

Table 2 describes the concentration of hydrogen discharged from the gas discharge pipe 5 after heat treatment and the recovery factor due to heating when the hydrocarbon reforming catalyst of each of the examples and the comparative examples was used. The recovery factor due to heating was defined by formula (5) below.

recovery factor due to heating=(hydrogen concentration after heat treatment−hydrogen concentration after deterioration due to sulfur)/equilibrium hydrogen concentration×100    (5)

The recovery factor determined by formula (5) being positive indicates that the hydrocarbon reforming catalyst that was deteriorated due to sulfur was recovered due to heat treatment.

After the test was completed, to examine presence or absence of carbon deposition, the hydrocarbon reforming <Initial Activity>

As described in Table 2, when the hydrocarbon reforming catalysts of examples 1 to 33 satisfying the requirements of the present invention were used, the equilibrium achievement percentage of the initial activity was 67% or more. On the other hand, when the hydrocarbon reforming catalysts of comparative examples 1 and 2 not satisfying the requirements of the present invention were used, the equilibrium achievement percentage of the initial activity was 37% or less and was a low value.

The reason for the hydrocarbon reforming catalyst satisfying the requirements of the present invention having high initial activity is conjectured to be that the complex oxide having at least a crystal phase containing $BaCeO_3$ as a primary component and having a perovskite structure is stabilized by containing dispersed Ru component in a solid solution state, aggregation and vaporization of the Ru component under a high-temperature oxidizing condition can be suppressed from occurring, and, as a result, the activity is improved.

On the other hand, regarding the hydrocarbon reforming catalysts of comparative examples not satisfying the requirements of the present invention, it is believed that since a crystal phase having a perovskite structure is not included, the above-described structure, i.e. a structure in which a Ru component in a solid solution state is dispersed in the complex oxide having a perovskite structure is not obtained, and the initial activity is reduced.

In addition, when the hydrocarbon reforming catalysts of examples 2 to 33 in which the molar ratio of Ru to Ba was 0.08 to 0.43, of the hydrocarbon reforming catalysts satisfying the requirements of the present invention, were used, the equilibrium achievement percentage of the initial activity was 96% or more and was a higher value. Therefore, regarding the hydrocarbon reforming catalysts satisfying the requirements of the present invention, the molar ratio of Ru to Ba is preferably 0.08 to 0.43.

<Sulfur Resistance>

As described in Table 2, when the hydrocarbon reforming catalysts of comparative examples 1 and 2 not satisfying the requirements of the present invention were used, the equilibrium achievement percentage after deterioration due to sulfur was 0%. On the other hand, when the hydrocarbon reforming catalysts of examples 1 to 33 satisfying the requirements of the present invention were used, the equilibrium achievement percentage of the initial activity after deterioration due to sulfur was 19% or more. It is conjectured that regarding the hydrocarbon reforming catalysts satisfying the requirements of the present invention, since Ru component in a solid solution state is dispersed in the complex oxide, the bonding force is strong, an effect of suppressing a poisoning component such as sulfur from adsorbing or forming a compound is obtained, and high sulfur resistance is provided.

In addition, when the hydrocarbon reforming catalysts of examples 1 to 28 in which the complex oxide has a first crystal phase containing $BaCeO_3$ as a primary component and a second crystal phase containing $BaZrO_3$ as a primary component were used, the equilibrium achievement percentage after deterioration due to sulfur was 44% or more and was a higher value. Therefore, regarding the hydrocarbon reforming catalysts satisfying the requirements of the present invention, it is preferable that the complex oxide further have a crystal phase containing $BaZrO_3$ as a primary component. The complex oxide having a perovskite structure further having a crystal phase containing $BaZrO_3$ as a primary component enables a catalyst function to be exerted for a long time even when sulfur impurities are contained in a raw material to be reformed.

<Recovery from Deterioration Due to Sulfur by Heating>

As described in Table 2, when the hydrocarbon reforming catalysts of examples 1 to 24 and 29 to 32 in which Y was contained in the complex oxide, of the hydrocarbon reforming catalysts satisfying the requirements of the present invention, were used, the recovery factor due to heating was a value higher than 0%. That is, regarding these hydrocarbon reforming catalysts, the catalyst function that was deteriorated due to sulfur was recovered by heat treatment.

Therefore, regarding the hydrocarbon reforming catalysts satisfying the requirements of the present invention, it is preferable that Y be contained in the complex oxide from the viewpoint of recovering the catalyst function that was deteriorated due to sulfur by heat treatment.

In addition, of the hydrocarbon reforming catalysts of examples 25 to 28 which satisfied the requirements of the present invention and in which the perovskite structure of the complex oxide was composed of at least Ba, Zr, Ce, and Ru without containing Y, regarding the hydrocarbon reforming catalysts of examples 27 and 28 in which the molar ratio of Ce to Ba was 0.50 to 0.70, the recovery factor due to heating was a value higher than 0%. Therefore, regarding the hydrocarbon reforming catalyst in which the perovskite structure of the complex oxide is composed of at least Ba, Zr, Ce, and Ru without containing Y, the molar ratio of Ce to Ba is preferably 0.50 to 0.70.

The hydrocarbon reforming catalyst that is recovered from deterioration due to sulfur by heating being used enables the catalyst function to be recovered by heat treatment from deterioration so as to continuously form a synthetic gas containing hydrogen and carbon monoxide from a hydrocarbon-based gas even in a reaction environment containing a sulfur component.

The present invention is not limited to the above-described embodiment and can be variously applied and modified within the scope of the present invention.

For example, the hydrocarbon reforming catalysts of the above-described examples take on granular forms. However, similarly to the common metal-supporting catalyst, a hydrocarbon reforming catalyst made into a powder may be supported by a ceramic or metal base material and be used. Alternatively, a catalyst powder may be formed by a method of press molding, extrusion molding, or the like without using a base material and be used in the form of a pellet, a ring, a honeycomb, or the like.

In the above-described embodiment, explanations are made with reference to the example in which a propane gas is used as the hydrocarbon-based gas, but the hydrocarbon-based gas is not limited to the propane gas.

REFERENCE SIGNS LIST 1 pipe
2 heating portion
3 hydrocarbon reforming catalyst
4 gas feed pipe
5 gas discharge pipe
6 hydrocarbon supply source
7 hydrogen outlet
100 hydrocarbon reforming apparatus

The invention claimed is:

1. A hydrocarbon reforming catalyst for forming a synthetic gas containing hydrogen and carbon monoxide from a hydrocarbon-based gas, the hydrocarbon reforming catalyst comprising:
   a complex oxide having a perovskite structure, the complex oxide having at least:
      a first crystal phase containing $BaCeO_3$ as a primary component,
      a second crystal phase containing $BaZrO_3$ as a primary component, and
      Ru.

2. The hydrocarbon reforming catalyst according to claim 1, wherein the perovskite structure is composed of at least Ba, Zr, Ce, and Ru.

3. The hydrocarbon reforming catalyst according to claim 1,
   wherein the complex oxide does not contain Y, and
   a molar ratio of Ce to Ba is 0.50 to 0.70.

4. The hydrocarbon reforming catalyst according to claim 1, wherein the complex oxide contains Y.

5. The hydrocarbon reforming catalyst according to claim 4, wherein the perovskite structure is composed of at least Ba, Zr, Ce, Y, and Ru.

6. The hydrocarbon reforming catalyst according to claim 5, wherein a molar ratio of the Ce to the Ba is 0.10 to 0.70.

7. The hydrocarbon reforming catalyst according to claim 5, wherein a molar ratio of the Ru to the Ba is 0.04 to 0.43.

8. The hydrocarbon reforming catalyst according to claim 7, wherein the molar ratio of the Ru to the Ba is 0.08 to 0.43.

9. The hydrocarbon reforming catalyst according to claim 5, wherein a molar ratio of the Y to the Ba is 0.05 to 0.50.

10. The hydrocarbon reforming catalyst according to claim 5, wherein a molar ratio of the Zr to the Ba is 0.1 to 0.80.

11. The hydrocarbon reforming catalyst according to claim 5, wherein a molar ratio of a total amount of the Zr, the Ce, and the Y to the Ba is 0.71 to 1.67.

12. The hydrocarbon reforming catalyst according to claim 5, wherein
a molar ratio of the Ce to the Ba is 0.10 to 0.70,
a molar ratio of the Ru to the Ba is 0.04 to 0.43,
a molar ratio of the Y to the Ba is 0.05 to 0.50,
a molar ratio of the Zr to the Ba is 0.1 to 0.80, and
a molar ratio of a total amount of the Zr, the Ce, and the Y to the Ba is 0.71 to 1.67.

13. A hydrocarbon reforming apparatus comprising:
a pipe through which a treatment object gas containing at least a hydrocarbon passes; and
the hydrocarbon reforming catalyst according to claim 1 disposed inside the pipe at a position so as to contact the treatment object gas passing therethrough.

14. The hydrocarbon reforming apparatus according to claim 13, wherein the perovskite structure is composed of at least Ba, Zr, Ce, and Ru.

15. The hydrocarbon reforming apparatus according to claim 13,
wherein the complex oxide does not contain Y, and
a molar ratio of Ce to Ba is 0.50 to 0.70.

16. The hydrocarbon reforming apparatus according to claim 13, wherein the complex oxide contains Y.

17. The hydrocarbon reforming apparatus according to claim 16, wherein the perovskite structure is composed of at least Ba, Zr, Ce, Y, and Ru.

18. A hydrocarbon reforming catalyst for forming a synthetic gas containing hydrogen and carbon monoxide from a hydrocarbon-based gas, the hydrocarbon reforming catalyst comprising:
a complex oxide having a perovskite structure, the complex oxide having at least a first crystal phase containing $BaCeO_3$ as a primary component, and also containing Ru,
wherein the complex oxide does not contain Y, and
a molar ratio of Ce to Ba is 0.50 to 0.70.

* * * * *